US012635853B2

(12) United States Patent
Komatsu

(10) Patent No.: US 12,635,853 B2
(45) Date of Patent: May 26, 2026

(54) ENDOSCOPE APPARATUS

(71) Applicant: HOYA CORPORATION, Tokyo (JP)

(72) Inventor: Masahiro Komatsu, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 510 days.

(21) Appl. No.: 17/772,818

(22) PCT Filed: Nov. 18, 2020

(86) PCT No.: PCT/JP2020/043073
§ 371 (c)(1),
(2) Date: Apr. 28, 2022

(87) PCT Pub. No.: WO2021/100783
PCT Pub. Date: May 27, 2021

(65) Prior Publication Data
US 2022/0369908 A1 Nov. 24, 2022

(30) Foreign Application Priority Data
Nov. 19, 2019 (JP) ................................. 2019-208887

(51) Int. Cl.
*A61B 1/00* (2006.01)
*A61B 1/04* (2006.01)
*H02J 50/10* (2016.01)
(52) U.S. Cl.
CPC ............ *A61B 1/00124* (2013.01); *A61B 1/04* (2013.01); *H02J 50/10* (2016.02)
(58) Field of Classification Search
CPC ............ A61B 1/00016; A61B 1/00029; A61B 1/00124; A61B 1/041; H02J 50/10; H02J 50/12
See application file for complete search history.

(56) References Cited

U.S. PATENT DOCUMENTS 11,211,822 B2 12/2021 Yamamoto et al.
2006/0116550 A1* 6/2006 Noguchi ............ A61B 1/00121
600/131

(Continued)

FOREIGN PATENT DOCUMENTS

CN 102395309 A 3/2012
JP 2010-252848 11/2010

(Continued)

OTHER PUBLICATIONS

Extended European Search Report issued in European application 20890062.1, dated Oct. 30, 2023.

(Continued)

*Primary Examiner* — Michael J Carey
*Assistant Examiner* — Stephen Floyd London
(74) *Attorney, Agent, or Firm* — Greenblum & Bernstein, P.L.C.

(57) ABSTRACT

An object, for an endoscope apparatus having a non-contact type connector, is to provide an endoscope apparatus that allows downsizing the connector and maintaining a stable coupling state. The endoscope apparatus includes an endoscope and a processor. The endoscope includes a connector. The processor includes a slot into which the connector is inserted. The processor is coupled to the endoscope. The slot has a first length in a width direction intersecting with an insertion direction in which the connector is inserted and has a second length larger than the first length in the insertion direction. The slot includes a transmission coil for transmitting electric power on a side surface of the slot. The connector includes a reception coil that receives the electric power from the transmission coil on a side surface of the connector.

10 Claims, 6 Drawing Sheets

(56)         References Cited

U.S. PATENT DOCUMENTS

| | | | |
|---|---|---|---|
| 2009/0215311 A1* | 8/2009 | Omori ............... | H01R 13/5227 |
| | | | 439/577 |
| 2012/0088970 A1 | 4/2012 | Kato et al. | |
| 2014/0015341 A1 | 1/2014 | Kagami et al. | |
| 2014/0184771 A1 | 7/2014 | Mazzetti et al. | |
| 2015/0222043 A1* | 8/2015 | Yagi ................... | H01R 13/6456 |
| | | | 439/625 |
| 2015/0272426 A1 | 10/2015 | Narita | |
| 2016/0341952 A1* | 11/2016 | Narita ............... | A61B 1/00124 |
| 2017/0014019 A1* | 1/2017 | Ogura ............... | A61B 1/00114 |
| 2017/0202437 A1* | 7/2017 | Hara .................. | A61B 1/00165 |
| 2017/0332884 A1* | 11/2017 | Amling .................. | H02J 50/10 |
| 2018/0090954 A1 | 3/2018 | Graham et al. | |
| 2018/0090996 A1* | 3/2018 | Kitamura ............... | A61C 17/22 |
| 2018/0090999 A1 | 3/2018 | Graham et al. | |
| 2022/0104692 A1* | 4/2022 | Deyanov ............ | A61B 1/00124 |

FOREIGN PATENT DOCUMENTS

| | | | | | |
|---|---|---|---|---|---|
| JP | 2012-200032 | | 10/2012 | | |
| JP | 2016-83308 | | 5/2016 | | |
| JP | 5978238 | | 8/2016 | | |
| JP | 2016-171667 | | 9/2016 | | |
| JP | 2018-535640 | | 11/2018 | | |
| JP | 2019-77372 | A | 5/2019 | | |
| JP | 2020-92963 | | 6/2020 | | |
| WO | WO-2011114771 | A1 * | 9/2011 | ......... | A61B 1/00124 |
| WO | 2015/145849 | | 10/2015 | | |
| WO | 2019/225167 | | 11/2019 | | |
| WO | WO-2019225167 | A1 * | 11/2019 | | |

OTHER PUBLICATIONS

International Search Report issued in International Bureau of WIPO Patent Application No. PCT/JP2020/043073, dated Feb. 2, 2021, along with an English translation thereof.

First Office Action issued in Chinese Application No. 202080074086.6, dated Jul. 19, 2024, together with an English translation.

Decision to Grant a Patent issued in Japanese application No. 2019-208887, dated Nov. 21, 2023, together with an English translation.

Office Action issued in European application No. EP20890062.1, dated Dec. 5, 2025.

* cited by examiner

A

B

A

B

C

ENDOSCOPE APPARATUS

TECHNICAL FIELD

The present invention relates to an endoscope apparatus.

BACKGROUND ART

An endoscope apparatus is generally configured of an endoscope having an insertion portion to be inserted into an inside of a body (for example, a digestive organ) of a subject and a processor coupled to the endoscope. The processor is configured to allow supplying electric power and light to the endoscope and exchanging various types of signals with the endoscope.

In the conventional endoscope apparatus, the endoscope and the processor are usually coupled by a contact type connector having an electrical contact point. However, recently, an endoscope apparatus configured to allow contactlessly transmitting and receiving electric power and various types of electric signals between the endoscope and the processor has been proposed (for example, see Patent Literature 1). The electric power is transmitted and received by, for example, transmitter and reception coils provided in the endoscope and the processor. The various types of electric signals are, for example, converted into optical signals once at the endoscope or the processor, transmitted and received via an optical communication port, and then converted again into the electric signals at the endoscope or the processor.

However, when the optical signals are transmitted and received through such a non-contact type connector, many transmission/reception ports are provided on the contact surface between the connector and the processor. In view of this, the area of the contact surface between the connector and the processor increases, and downsizing of the connector is difficult. The increased area of the contact surface between the connector and the processor causes the connector to be flapped by up-and-down and right-and-left movement of the endoscope, and a coupling state between the connector and the processor may become unstable.

CITATION LIST

Patent Literature

Patent Literature 1: Japanese Patent No. 5978238

SUMMARY OF INVENTION

Technical Problem

An object of the present invention is to provide, for an endoscope apparatus having a non-contact type connector, an endoscope apparatus that allows downsizing the connector and maintaining a stable coupling state.

Solution to Problem

In order to solve the problems, an endoscope apparatus according to the present invention comprises an endoscope and a processor. The endoscope includes a connector. The processor includes a slot into which the connector is inserted. The processor is coupled to the endoscope. The slot has a first length in a width direction intersecting with an insertion direction in which the connector is inserted and has a second length larger than the first length in the insertion direction. The slot includes a transmission coil for transmitting electric power on a side surface of the slot. The connector includes a reception coil that receives the electric power from the transmission coil on a side surface of the connector.

Advantageous Effects of Invention

According to the endoscope of the present invention, for an endoscope apparatus having a non-contact type connector, an endoscope apparatus that allows downsizing the connector and maintaining a stable coupling state can be provided.

DESCRIPTION OF EMBODIMENTS

In the following, the present embodiments will be described with reference to the attached drawings. In the attached drawings, functionally identical elements may be designated with identical numerals. While the attached drawings illustrate embodiments and implementation examples in accordance with the principle of the present disclosure, the embodiments and implementation examples are provided to aid in understanding the present disclosure and should not be interpreted as limiting the present disclosure. The descriptions provided herein are merely illustrations of typical examples and are not intended as limiting in anyway the scope of the claims of the present disclosure or application examples thereof.

The embodiments will be described in such sufficient detail as to enable those skilled in the art to carry out the present disclosure. However, it should be understood that other implementations and modes are also possible, and that various modifications of configurations and structures and substitutions of various elements are possible without departing from the scope and spirit of the technical concepts of the present disclosure. Accordingly, the following descriptions are not to be regarded as limiting.

First Embodiment

Figure 1:
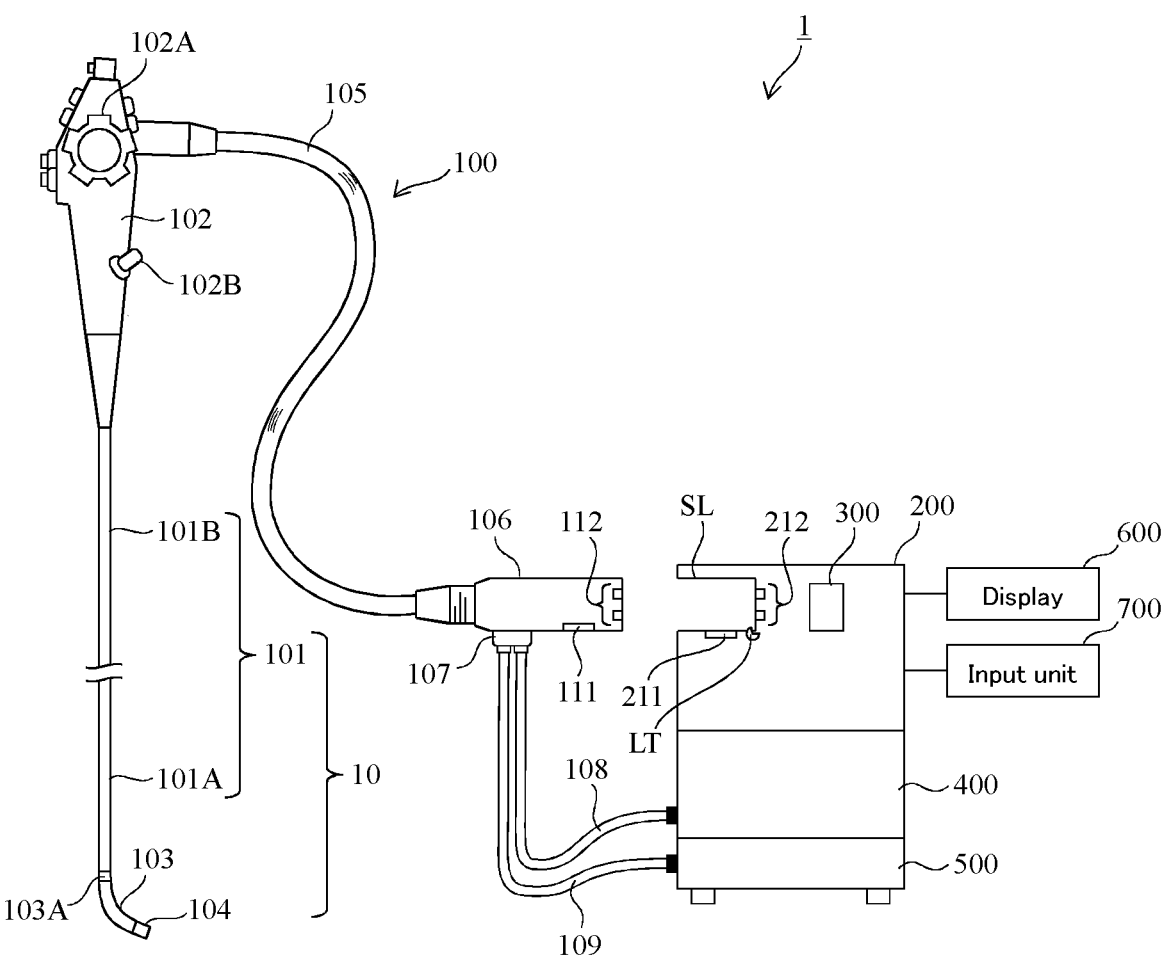
FIG. 1 is an external view of an endoscope apparatus 1 according to a first embodiment.
Figure 2:
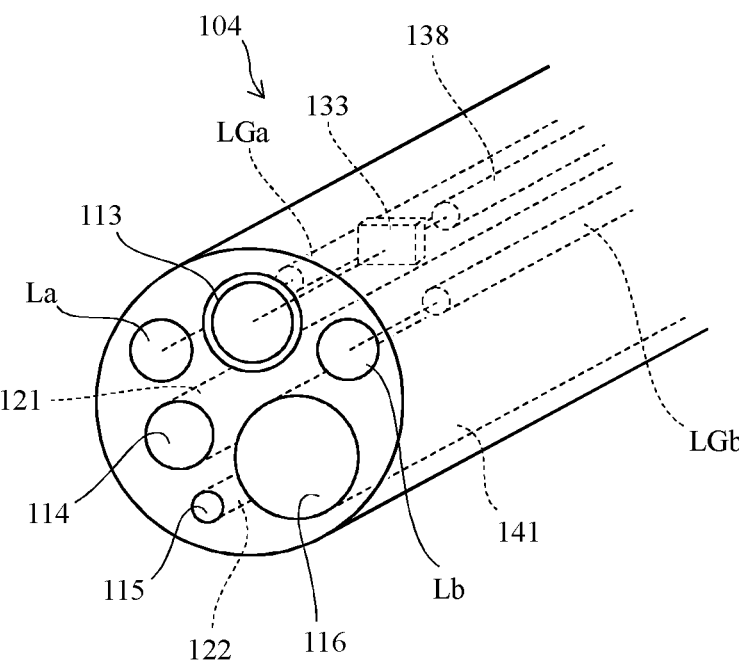
FIG. 2 is a schematic perspective view describing a structure of a distal end portion 104 part of an endoscope 100 according to the first embodiment.

First, an endoscope apparatus according to a first embodiment of the present invention will be described in detail. FIG. 1 is an external view of an endoscope apparatus 1 according to the first embodiment. FIG. 2 is a perspective view describing a structure of a distal end portion 104 of an endoscope 100. The endoscope apparatus 1 is primarily configured of the endoscope 100, a processor 200, a light source device 300, a water supply/air supply unit 400, a suction unit 500, a display 600, and an input unit 700.

The endoscope 100 is configured to be insertable into a body of a subject and has a function of capturing an image of a photographic subject and transmitting an image signal of the captured image to the processor 200. The processor 200 receives the image signal from the endoscope 100 and performs predetermined signal processing.

The light source device 300 is configured to be couplable to the processor 200 and internally includes a light source unit that emits irradiated light with which the photographic subject is irradiated. The subject is irradiated with the light from the light source unit via a light guide described later. The light source device 300 may be configured to be separated from the processor 200 and configured to be couplable to the processor 200, or may be embedded into processor 200.

The water supply/air supply unit 400 includes an air pump (not illustrated) to discharge a water flow or an airflow supplied to the subject. The suction unit 500 includes a pump and a tank (not illustrated) to suction a bodily fluid and a resected substance suctioned from the inside of the body of the subject via the endoscope 100.

The display 600 is a display device to perform display based on, for example, a data processing result by the processor 200. The input unit 700 is a device to input commands from an operator in various kinds of measurement operations.

The endoscope 100 includes an insertion portion 10, a hand operating unit 102, a universal cable 105, and a connector 106. The insertion portion 10 further includes a flexible tube portion 101, a curving portion 103, and a distal end portion 104.

As illustrated in FIG. 1, the insertion portion 10 of the endoscope 100 has flexibility and includes the flexible tube portion 101 to be inserted into the body of the subject. The flexible tube portion 101 has one end coupled to the hand operating unit 102. Besides, the hand operating unit 102 includes, for example, a curving operation knob 102A and an operation unit operable by a user. The hand operating unit 102 is a part to cause the operator to perform various types of operations for capturing an image by the endoscope apparatus 1. A treatment instrument insertion port 102B for inserting a treatment instrument is provided to the hand operating unit 102.

In the flexible tube portion 101, a part close to the curving portion 103 is a first flexible tube portion 101A and a part close to the hand operating unit 102 is a second flexible tube portion 101B. While the curving portion 103 is configured to be actively changeable in shape by the operation of the operator of the curving operation knob 102A, the first flexible tube portion 101A is a part that passively changes in shape by an external force unrelated to the operation of the curving operation knob 102A, for example an external force generated by the distal end portion 104 and the curving portion 103 coming into contact with a wall surface of a digestive organ. Although the same applies to the second flexible tube portion 101B, the second flexible tube portion 101B has a small degree of change in shape compared with the first flexible tube portion 101A (the maximum curvature radius is large). In the example of FIG. 1, while the flexible tube portion 101 has two types of flexible tube portions, the flexible tube portion 101 is not limited to this. Three types or more flexible tube portions may be included, or one type may be included.

The curving portion 103 (active curving portion) configured to be curved is disposed at the distal end of the flexible tube portion 101. As described above, pulling an operation wire (not illustrated in FIG. 1) in conjunction with a rotating operation of the curving operation knob 102A disposed on the hand operating unit 102 curves the curving portion 103. Between the curving portion 103 and the first flexible tube portion 101A, a coupling portion that does not deform by a curving wire W or an external force may be disposed.

Further, the distal end portion 104 that includes an imaging device (an imaging unit) is joined to the distal end of the curving portion 103. The direction of the distal end portion 104 changes according to the curving operation of the curving portion 103 by the rotating operation of the curving operation knob 102A, thus allowing change of the photographed area by the endoscope 100.

The universal cable 105 extends from the opposite side of the hand operating unit 102 to the connector 106. Similarly to the insertion portion 10, the universal cable 105 internally includes a light guide, various types of wirings, and various types of tubes.

The connector 106 is a coupling member for coupling the endoscope 100 to the processor 200. The connector 106 can be secured to the processor 200 by a latch LT after being inserted into a slot SL provided in the processor 200 and inserted to a predetermined position. The connector 106 includes a water supply/air supply tube 108 as a passage to transmit a water flow and an airflow to the insertion portion 10 and a suction tube 109 for suction.

The connector 106 is configured to allow contactlessly transmitting and receiving electric power, light, and various types of signals with the processor 200. Specifically, the connector 106 includes a reception coil 111 on the side surface of the connector 106. The reception coil 111 is arranged at a position of being opposed to a transmission coil 211 disposed on the side surface of the processor 200 when the connector 106 is inserted into the slot SL. The connector 106 receives the electric power supplied to the transmission coil 211 via the reception coil 111.

The connector 106 includes an optical transmission/reception port 112 for optical communication at the distal end portion of the connector 106. The optical transmission/reception port 112 works with a light emitting device and a light receiving device (not illustrated). The light transmission/reception port 112 is arranged at a position of being opposed to an optical transmission/reception port 212 arranged on the far side (bottom surface) of the slot SL by inserting the connector 106 into the slot SL. Similarly, the optical transmission/reception port 212 works with a light emitting device and a light receiving device (not illustrated). Although not illustrated in the drawing, the connector 106 also includes an optical fiber for transmitting the light from the light source device 300 to the insertion portion 10 and an optical connector for optical incidence to the optical fiber.

With reference to FIG. 2, a structure of the distal end portion 104 of the endoscope 100 will be described. Light distribution lenses La and Lb are arranged at the distal end portion 104 of the endoscope 100, and light guides LGa and LGb extend across from the distal end portion 104 to the connector 106. The light from the light source device 300 is guided by the light guides LGa and LGb, and the subject is irradiated with the light by the light distribution lenses La and Lb arranged at the distal end portion 104.

As illustrated in FIG. 2, the endoscope 100 includes an objective lens 113 and an imaging device 133 in the distal end portion 104. The objective lens 113 disposed in the distal end portion 104 condenses scattered light and reflected light from the subject to form an image of the subject on a photo-receiving surface of the imaging device 133.

As one example, the imaging device 133 can be constituted of a Charge Coupled Device (CCD) or a Complementary Metal Oxide Semiconductor Sensor (a CMOS sensor). The imaging device 133 is controlled by a signal (such as a gain control signal, an exposure control signal, and a shutter speed control signal) supplied from the processor 200 via an electrical wiring 138 and supplies an image signal of the captured image to the processor 200 via the electrical wiring 138 and an A/D converter circuit (not illustrated). Electric signals transmitted and received via the electrical wiring 138 are converted into optical signals, and then transmitted and received between the endoscope 100 and the processor 200 via an above-described light transmitting units W1 and W2.

An air supply/water supply port 114, an auxiliary water supply port 115, and a treatment instrument port 116 are provided as end portions or openings of the various types of tubes in the end surface of the distal end portion 104. The air supply/water supply port 114 (nozzle) is coupled to an air supply/water supply tube 121 to introduce the water flow or the airflow for, for example, cleaning the distal end portion 104.

The auxiliary water supply port 115 is coupled to an auxiliary water supply tube 122 to introduce auxiliary supply water to remove excrement within the visual field. The tubes 121 to 122 are disposed so as to extend along inside the distal end portion 104, the curving portion 103, the flexible tube portion 101, the hand operating unit 102, and the universal cable 105.

In addition to the tubes 121 to 122, the endoscope 100 internally includes a treatment instrument tube 141. A treatment instrument, such as forceps, is provided inside the treatment instrument tube 141 to freely advance and retreat. A distal end of the treatment instrument tube 141 constitutes the treatment instrument port 116 in the distal end portion 104.

Figure 3:
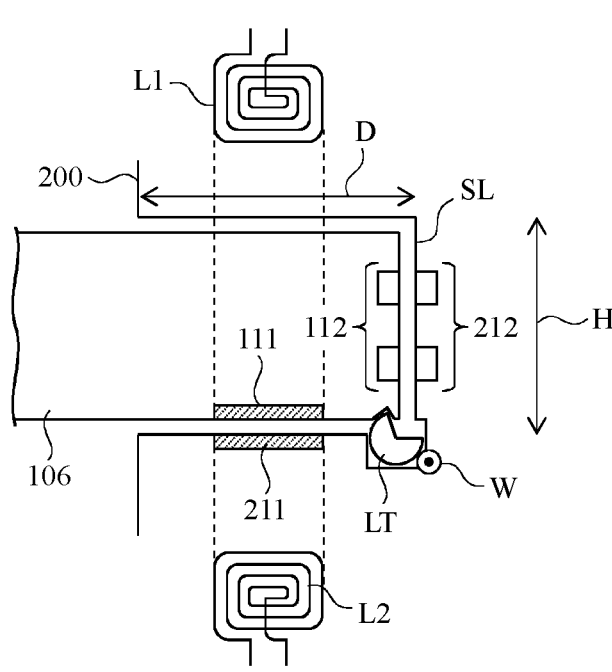
FIG. 3 is schematic cross-sectional views describing a configuration of a slot SL and a connector 106 according to the first embodiment.
Figure 3:
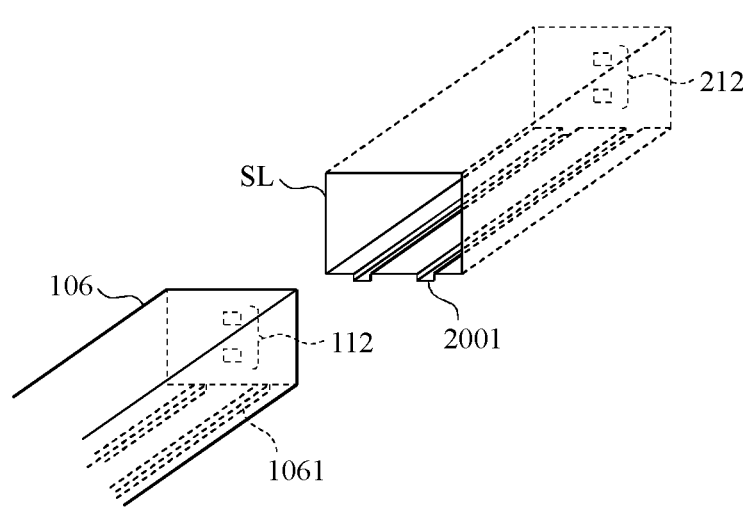

With reference to FIG. 3, a configuration of the slot SL and the connector 106 will be described. As described above, the reception coil 111 for receiving electric power is arranged on the side surface of the connector 106. The reception coil 111 can be configured of a winding coil L1 as illustrated in FIG. 3, A. On the other hand, the transmission coil 211 for transmitting electric power to the winding coil L1 is arranged on the side surface of the slot SL. The transmission coil 211 can be configured of a winding coil L2 as illustrated in FIG. 3, A. The electric power provided to the transmission coil 211 can be transmitted to the reception coil 111 by electromagnetic induction.

As illustrated in FIG. 3, B, the connector 106 has a linear sliding rail 1061 extending toward an insertion direction of the connector 106 on the lower surface of the connector 106. A sliding groove 2001 into which the sliding rail 1061 is inserted is formed on the lower surface of the slot SL. The connector 106 slides inside the slot SL in a state where the sliding rail 1061 is inserted into the sliding groove 2001, thus allowing the connector 106 to linearly move inside the slot SL.

Here, the slot SL has dimensions of a length D in a depth direction (insertion direction of the connector 106), a length H in a height direction perpendicular to the depth direction, and a length W in a width direction intersecting with the depth direction. The length D is larger than H and W, and preferably D is 1.5 times or more of H and W. The connector 106 that is inserted into the slot SL has a shape corresponding to the slot SL in the inserted portion.

Thus, in the endoscope apparatus according to the first embodiment, the slot SL and the insertion portion of the connector 106 have a vertically elongate shape that is long in the depth direction. Having the vertically elongate shape reduces a possibility that the connector 106 is shaken right to left and varies in position even in a case where, for example, the endoscope 100 is shaken up and down and right to left, which causes force to be applied to the connector 106.

In the first embodiment, the coils 111 and 211 for transmitting and receiving electric power are arranged on the side surfaces of the connector 106 and the slot SL. Arranging the reception coil 111 and the transmission coil 211 on the side surfaces allows for increasing an area on which other transmission/reception ports are arranged at the front end of the connector 106 by the amounts of the coils 111 and 211. Further, forming the reception coil 111 and the transmission coil 211 on the side surfaces of the connector 106 and the slot SL allows for transmitting and receiving the electric power between both sides not only in a stage where the insertion and securing of the connector 106 is completed but also from the middle of the insertion operation. In view of this, the timing of starting electric power supply from the processor 200 to the endoscope 100 can be made sooner compared with that in the prior art.

Second Embodiment

Next, an endoscope apparatus according to a second embodiment will be described with reference to FIG. 4 and FIG. 5. Since the constituent elements in FIG. 4 and FIG. 5 that are identical to those in FIG. 1 and FIG. 3 are denoted by the identical reference numerals in FIG. 1, the overlapping descriptions will be omitted.

Figure 4:
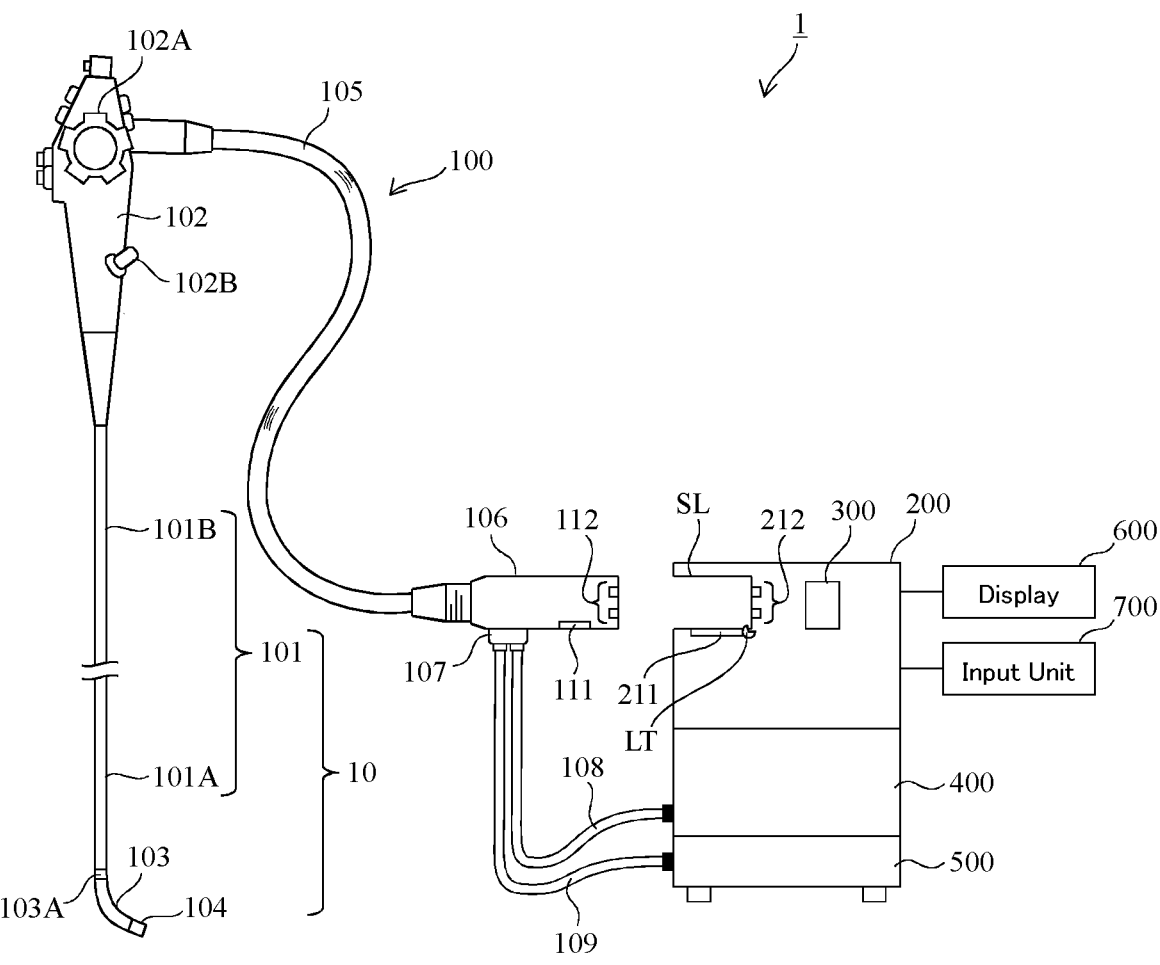
FIG. 4 is an external view of an endoscope apparatus according to a second embodiment.
Figure 5:
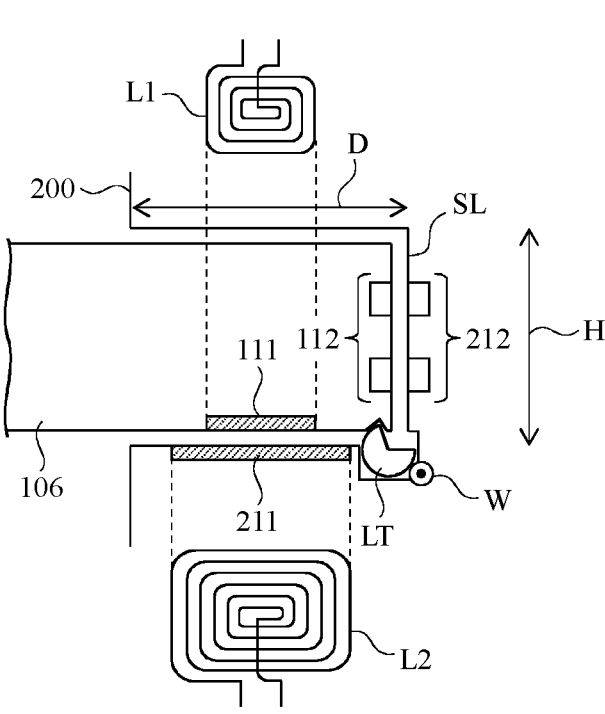
FIG. 5 is a schematic cross-sectional views describing a configuration of the slot SL and the connector 106 according to the second embodiment.

As illustrated in FIG. 4 and FIG. 5, in the endoscope apparatus according to the second embodiment, the area of the transmission coil 211 is made larger than the area of the reception coil 111. This makes it easier to receive the electromagnetic induction from the transmission coil 211 compared with the first embodiment. As illustrated in FIG. 5, in a state where the securing of the connector 106 is completed, it is preferred that the reception coil 111 including the front end and the rear end thereof is completely encompassed by the transmission coil 211, and one end of the transmission coil 211 on the inlet side of the slot SL is closer to the inlet side of the slot SL than one end of the reception coil 111. This can accelerate the timing when the electric power transmission to the connector 106 starts and accelerate an activation of the endoscope apparatus 1.

Third Embodiment

Next, an endoscope apparatus according to a third embodiment will be described with reference to FIG. 6. Since the constituent elements in FIG. 6 that are identical to those in FIG. 3 are denoted by the identical reference numerals in FIG. 1, the overlapping descriptions will be omitted.

Figure 6:
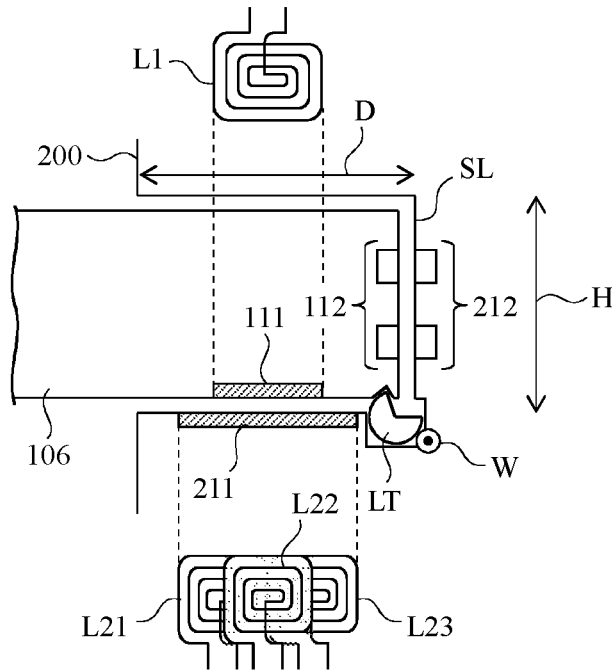
FIG. 6 is a schematic cross-sectional view describing a configuration of the slot SL and the connector 106 according to a third embodiment.

As illustrated in FIG. 6, in the endoscope apparatus according to the third embodiment, the transmission coil 211 includes a plurality of (for example, three) coils L21 to L23. The plurality of coils L21 to L23 are arrayed along the insertion direction of the connector 106. The plurality of coils L21 to L23 may be arrayed in a form of being partly overlapped as illustrated in FIG. 6 or may be arrayed at a predetermined interval.

In addition, similarly to the second embodiment, the total area of the transmission coil 211 is made larger than the total area of the reception coil 111. This makes it easier to receive the electromagnetic induction from the transmission coil 211 compared with the first embodiment. As illustrated in FIG. 6, in a state where the securing of the connector 106 is completed, it is preferred that the reception coil 111 including the front end and the rear end thereof is completely encompassed by the transmission coil 211, and one end of the transmission coil 211 on the inlet side of the slot SL is closer to the inlet side of the slot SL than one end of the reception coil 111. This can accelerate the timing when the electric power transmission to the connector 106 starts and accelerate an activation of the endoscope apparatus 1.

The electric power supplied to the coils L21 to L23 may all be identical or may be different from one another. For example, the coil L22 in the center may be supplied with large electric power compared with the other coils L21 and L23. The timing when the electric power is supplied may also be different from one another between the coils L21 to L23.

Figure 7:
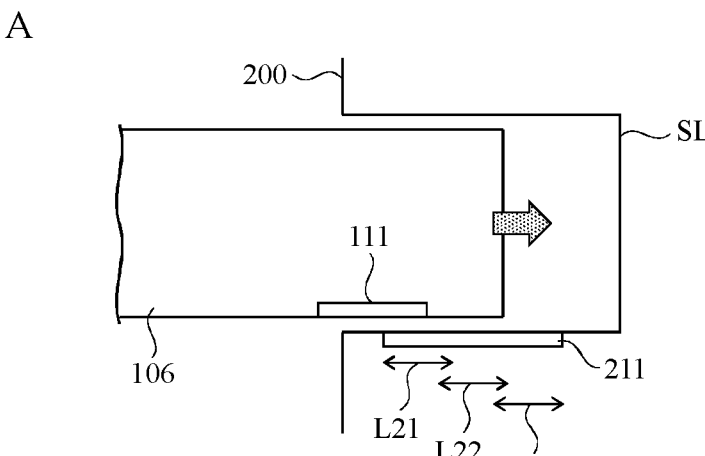
FIG. 7 is schematic diagrams describing an operation of an endoscope apparatus according to the third embodiment.
Figure 7:
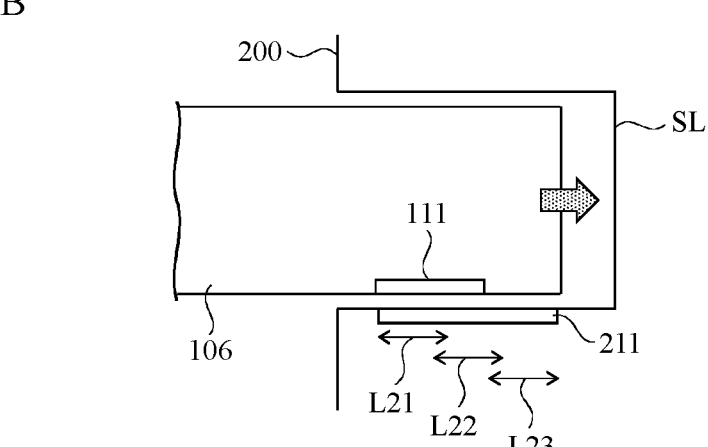
Figure 7:
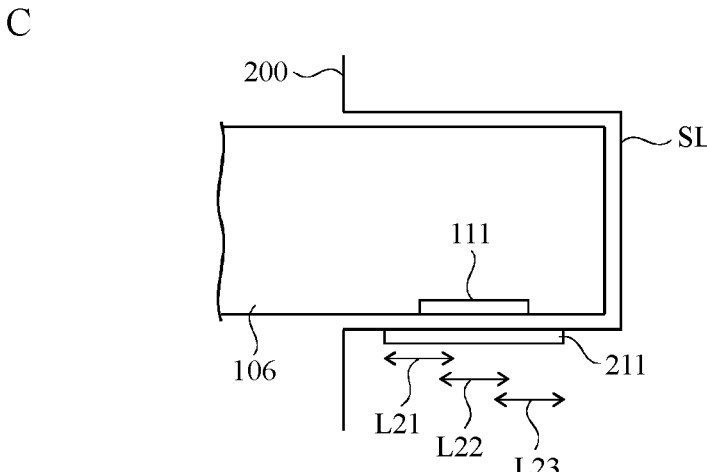

With reference to FIG. 7, an operation according to the third embodiment will be described. FIGS. 7, A to C illustrate a state where the connector 106 is inserted into the slot SL and gradually progresses in the depth direction in chronological order. As illustrated in FIG. 7, in A, even in a case where the front end of the connector 106 is still near the inlet of the slot SL, the coil L21 in the transmission coil 211 and the reception coil 111 are in a state of being overlapped, and the supply of electric power from the processor 200 to the endoscope 100 can be started. The endoscope 100 can start, for example, an initial setting operation by the start of the electric power supply.

Further, as illustrated in FIG. 7, in B, when the connector 106 further progresses in the depth direction of the slot SL, the electromagnetic induction is received not only from the coil L21 but also from the coil L22 positioned further on the far side, and the supply of more electric power to the endoscope 100 can be started. Then, as illustrated in FIG. 7, in C, when the front end of the connector 106 reaches the far side of the slot SL and the connector 106 is secured by the latch LT, the supply of electric power from all the coils L21 to L23 can be started.

As described above, the connector 106 linearly moves inside the slot SL along the sliding rail 1061 and groove 2001. In view of this, the optical transmission/reception ports 112 and 212 can be in a communicable state before the connector 106 is secured to a final position. For example, since the optical transmission/reception ports 112 and 212 are linearly aligned even in a state as illustrated in FIG. 7, A and B, light can be transmitted and received. The optical communication is performed using the received electric power before the state in FIG. 7, C is obtained, and for example, initial setting of the endoscope 100 and the like can be started. Thus, since the initial setting can be completed while the connector 106 is being prepared for coupling, performance of the endoscope apparatus can be improved.

OTHERS

The present invention is not limited to the above-described embodiments, and includes various modifications. For example, the above-described embodiments are described in detail for ease of understanding of the present invention, and does not necessarily include all of the described configurations. A part of the configuration of one embodiment can be replaced by the configuration of another embodiment. The configuration of another embodiment can be added to the configuration of one embodiment. Addition, deletion, or replacement of another configuration can be performed on a part of the configuration in each of the embodiments.

| Reference Signs List | |
| --- | --- |
| 1 | Endoscope apparatus |
| 100 | Endoscope |
| 10 | Insertion portion |
| 101 | Flexible tube portion |
| 101A | First flexible tube portion |
| 101B | Second flexible tube portion |
| 102 | Hand operating unit |
| 102A | Curving operation knob |
| 103 | Curving portion |
| 104 | Distal end portion |
| 105 | Universal cable |
| 106 | Connector |
| SL | Slot |
| 108 | Water supply/air supply tube |
| 109 | Suction tube |
| 211 | Transmission coil |
| 111 | Reception coil |
| LGa, LGb | Light guide |
| La, Lb | Light distribution lens |
| 113 | Objective lens |
| 114 | Air supply/water supply port |
| 115 | Auxiliary water supply port |
| 116 | Treatment instrument port |
| 121 | Air supply/water supply tube |
| 122 | Auxiliary water supply tube |
| 141 | Treatment instrument tube |
| 133 | Imaging device |
| 138 | Electrical wiring |
| 200 | Processor |
| 300 | Light source device |
| 400 | Water supply/air supply unit |
| 500 | Suction unit |
| 600 | Display |
| 700 | Input unit |

The invention claimed is:

1. An endoscope apparatus comprising:

an endoscope including a connector having a first optical transmission/reception port at a distalmost end portion of the connector;

a processor including a slot into which the connector is inserted in an insertion position, the processor being coupled to the endoscope; and a latch configured to latch the connector to the slot in the insertion position to a latched position, wherein the slot has a first length in a width direction intersecting with an insertion direction in which the connector is inserted and has a second length larger than the first length in the insertion direction, wherein the slot includes:

a transmission coil for transmitting electric power on a side surface of the slot, and a pair of sliding grooves having a flat lower surface and extending in the insertion direction and formed on a lower surface of the slot, and a second optical transmission/reception port at a position opposed to the first optical transmission/reception port on a far side end surface of the slot such that signals are contactlessly exchangeable between the endoscope and the processor, and wherein the connector includes:

a reception coil that receives the electric power from the transmission coil on a side surface of the connector, and a pair of linear sliding rails extending along a flat surface in the insertion direction and being respectively insertable into the pair of sliding grooves, and wherein in the latched position, a gap is present between an entirety of the distalmost end portion of the connector and the far side end surface of the slot.

2. The endoscope apparatus according to claim 1, wherein the transmission coil has a larger area than the reception coil.

3. The endoscope apparatus according to claim 1, wherein the transmission coil includes a plurality of coils arrayed along the insertion direction.

4. The endoscope apparatus according to claim 3, wherein the transmission coil has a larger area than the reception coil.

5. The endoscope apparatus according to claim 3, wherein the plurality of coils are arrayed along the insertion direction in a form of being partly overlapped.

6. The endoscope apparatus according to claim 1, wherein the transmission coil has a larger area than the reception coil.

7. The endoscope apparatus according to claim 1, wherein the transmission coil includes a plurality of coils arrayed along the insertion direction.

8. The endoscope apparatus according to claim 7, wherein the transmission coil has a larger area than the reception coil.

9. The endoscope apparatus according to claim 7, wherein the plurality of coils are arrayed along the insertion direction in a form of being partly overlapped.

10. The endoscope apparatus according to claim 1, wherein the pair of linear sliding rails is formed on an underside of the connector.

* * * * *